United States Patent [19]
Kino et al.

[11] Patent Number: 5,656,299
[45] Date of Patent: Aug. 12, 1997

[54] SUSTAINED RELEASE MICROSPHERE PREPARATION CONTAINING ANTIPSYCHOTIC DRUG AND PRODUCTION PROCESS THEREOF

[75] Inventors: Shigemi Kino; Tomonori Osajima; Hiroaki Mizuta, all of Fukuoka, Japan

[73] Assignee: Yoshitomi Pharmaceutical Industries, Ltd., Osaka, Japan

[21] Appl. No.: 443,021

[22] Filed: May 17, 1995

Related U.S. Application Data

[63] Continuation-in-part of PCT/JP93/01673, Nov. 15, 1993.

[30] Foreign Application Priority Data

Nov. 17, 1992 [JP] Japan ................ 4-332441

[51] Int. Cl.⁶ ............................................. A61K 9/50
[52] U.S. Cl. ..................... 424/489; 424/490; 424/497; 424/426
[58] Field of Search ........................... 424/426, 490, 424/497, 489, 529, 530; 514/938

[56] References Cited

U.S. PATENT DOCUMENTS

| | | | |
|---|---|---|---|
| 3,773,919 | 11/1973 | Boswell et al. | 424/19 |
| 4,389,330 | 6/1983 | Tice et al. | 427/213.36 |
| 4,940,588 | 7/1990 | Sparks et al. | 424/490 |
| 4,994,281 | 2/1991 | Maranishi et al. | 424/497 |
| 5,008,114 | 4/1991 | Lovrecich | 424/484 |

OTHER PUBLICATIONS

Microencapsulation And Dissolution Properties Of A Neuroleptic In A Biodegradable Polymer, Poly (d,l–lactide), *Journal of Pharmaceutical Sciences*, by Suzuki and Price, vol. 74, No.1, 21–24, Jan. 1985.
Chemical Abstracts, vol. 117, No. 24, 14 Dec. 1992.
Chemical Abstracts, vol. 102, No. 18, 6 May 1985.
Chemical Abstracts, vol. 106, No. 6, 9 Feb. 1987.
International Search Report.

*Primary Examiner*—Thurman K. Page
*Assistant Examiner*—Sharon Howard
*Attorney, Agent, or Firm*—Sughrue, Mion, Zinn, Macpeak & Seas

[57] ABSTRACT

A sustained release microsphere preparation which is produced by including a hydrophobic antipsychotic drug such as bromperidol, haloperidol or the like into a base composed of a high molecular weight polymer having in vivo histocompatibility such as polylactic acid, poly(lactic-co-glycolic)acid or the like, and a process for the production thereof.

4 Claims, 4 Drawing Sheets

SUSTAINED RELEASE MICROSPHERE PREPARATION CONTAINING ANTIPSYCHOTIC DRUG AND PRODUCTION PROCESS THEREOF

This is a continuation-in-part application of PCT/JP93/01673, filed Nov. 15, 1993.

1. Technical Field

This invention relates to a sustained release microsphere preparation which contains a hydrophobic antipsychotic drug and to a process for producing the preparation.

2. Background Art

It is said that, in the drug therapy of mental diseases, maintenance therapy by continuous administration is effective in preventing recidivism of symptoms, whereby it is possible to guide patients in their daily lives. However, since the current maintenance therapy with antipsychotic drugs is carried out by orally administering tablets or fine granules once a day or dividing the daily dose into several doses per day, decreased patient compliance during the maintenance therapy causes recidivism of symptoms or re-hospitalization. Consequently, current maintenance therapy has a drawback in that certain means must be employed to improve compliance after rehabilitation or during outpatient maintenance therapy.

In order to resolve this problem, long acting injections containing drugs in the form of decanoic acid ester or enanthic acid ester have been used. For example, decanoic acid esters of haloperidol and bromperidol are disclosed in JP-A-56-8318 (the term "JP-A" as used herein means "unexamined published Japanese Patent Application"), and decanoic acid ester or enanthic acid ester of fluphenazine is also known and used in this therapeutic field.

However, these prior art long acting injections have drawbacks in that their administration route is limited to intramuscular injection, resistance at the time of administration is large because they are oil injections while the dispersibility of oil in muscular tissue is low, and their administration gives patients severe pain. In addition, there is a possibility that their effects may vary depending on individuals and their ages because, though the esters of active ingredients show a sustained release effect in the living body by gradually releasing their active moieties due to the influence of esterase, release of drugs in the living body generally depends on their transition rate from, the administered site into the lymphoid system and also on enzyme activity. Accordingly, it is desirable to develop new long acting injections in which the drugs themselves as opposed to their esters can be used.

On the other hand, each of JP-A-62-201816, JP-B-1-57087 and JP-B-2-124814 (the term "JP-B" as used herein means "examined Japanese Patent Publication") discloses sustained release microcapsules which make possible the administration of water soluble drugs at an interval of once a week or once a month, and production processes therefor. Also, JP-A-55-33414 discloses a so-called in-water drying method in which a hydrophobic drug and a polylactic acid are dissolved in a common organic solvent, the resulting solution is emulsified by adding a phase separation agent and then the solvent is removed by evaporation to obtain fine particles.

U.S. Pat. No. 4,994,281 discloses polylactic acid microspheres, prepared by the in-water drying method, containing a physiologically active substance (haloperidol, chlorpromazine, etc.) and having an average particle size of about 0.1 to 10 μm.

SUMMARY OF THE INVENTION

With the aim of improvement in compliance at the time of maintenance therapy with hydrophobic antipsychotic drugs, the present inventors have conducted intensive studies on the development of a sustained release pharmaceutical preparation in which a drug itself is used as an active ingredient without modification. As the result, it was found that a drug can be released at an almost constant rate extending over 1 week or more by including a hydrophobic antipsychotic drug in the form of microcrystals having an average particle size of 10 μm or less, desirably 5 μm or less, into a base comprising a biodegradable high molecular weight polymer having in vivo histocompatibility to make a sustained release microsphere preparation and administrating it by subcutaneous or intramuscular injection, hence resulting in the accomplishment of the present invention.

Accordingly, the present invention relates to (1) an antipsychotic drug-containing sustained release microsphere preparation which is produced by including a hydrophobic antipsychotic drug in the form of microcrystals of the above-noted size into a base comprising a high molecular weight polymer having in vivo histocompatibility and (2) a process for producing an antipsychotic drug-containing sustained release microsphere preparation which comprises making an oil layer comprising a solution of a high molecular weight polymer having in vivo histocompatibility containing said hydrophobic antipsychotic drug microcrystals, adding the oil layer to a water layer, subjecting the resulting mixture to an emulsification treatment to obtain an O/W type emulsion and subsequently removing the solvent in the oil layer by the in-water drying method.

In another and preferred embodiment of the present invention, the resulting microspheres, following any necessary size screening, have an average particle size of about 0.5 to 400 μm, more preferably about 0.5 to 200 μm, most preferably about 15 to 50 μm.

DETAILED DESCRIPTION OF THE INVENTION

The hydrophobic antipsychotic drug to be applied to the present invention is selected from haloperidol, bromperidol, fluphenazine, chlorpromazine, sulpiride, carpipramine, clocapramine, mosapramine, risperidone, clozapine, oranzapine and sertindole and pharmaceutically acceptable acid addition salts thereof, preferably from the group consisting of haloperidol, bromperidol, fluphenazine maleate, chlorpromazine, chlorpromazine hibenzoate, sulpiride, carpipramine hydrochloride, carpipramine maleate, clocapramine hydrochloride, mosapramine hydrochloride, risperidone, clozapine, oranzapine and sertindole, of which haloperidol or bromperidol is particularly preferred.

The base that constitutes the sustained release microspheres of the present invention should have such a function that its concentration in blood plasma can be maintained at a constant level by a single administration whereby its effects can be obtained stably over a prolonged period of time. A biodegradable high molecular weight polymer having in vivo histocompatibility is used as a base having such a function. The sustained release microspheres of the present invention are constructed in the manner that the hydrophobic antipsychotic drug is included therein. Examples of such a high molecular weight polymer having in vivo histocompatibility include polymers of fatty acid esters or copolymers thereof, polyacrylic esters, polyhydroxybutyric acids, polyalkylene oxalates, polyorthoesters, polycarbonates and polyamino acids, which may be used alone or as a mixture of two or more. Illustrative examples of the polymers fatty acid esters or copolymers thereof include polylactic acid, polyglycolic acid, polycitric acid, polymalic acid and poly (lactic-co-glycolic)acid, which may also be used alone or as a mixture of two or more. Other useful examples include poly-α-cyanoacrylic ester, poly-β-hydroxybutyric acid, polytrimethylene oxalate, polyorthoester, polyorthocarbonate, polyethylene carbonate, poly γ-benzyl-L-glumatic acid and poly L-alanine, which may be used alone or as a mixture of two or more. Of these polymers polylactic acid, polyglycolic acid or poly(lactic-co-glycolic) acid may be preferred.

These in vivo histocompatibility high molecular weight polymers to be used in the present invention may have an average molecular weight of preferably from about 2,000 to about 80,000, more preferably from about 5,000 to about 20,000. When poly(lactic-co-glycolic)acid is used as the in vivo histocompatibility high molecular weight polymer, compositional ratio of lactic acid and glycolic acid may be in the range of from about 100:0 to 50:50, preferably at 75:25 and 50:50.

Although the amount of the high molecular weight polymer(s) is decided by the drug-releasing rate, period and the like, and may be controlled within in a range of from about 0.2 to about 10,000 times by weight of the drug, it is preferred that the high molecular weight polymer is used as the base of the microsphere preparation of the present invention in an amount of from 1 to 1,000 times by weight of the drug.

A solution containing the above high molecular weight polymer (oil layer) is prepared by dissolving the high molecular weight polymer in a solvent. The concentration of the high molecular weight polymer in the oil layer may be in the range of preferably from about 0.5 to about 90% (w/w), more preferably from about 2 to about 60% (w/w).

Examples of the solvent include those which have a boiling point of about 120° C. or lower, do not show miscibility with water and can dissolve high molecular weight polymers, such as alkane halides (dichloromethane, chloroform, chloroethane, dichloroethane, trichloroethane and the like), ethyl acetate, ethyl ether, cyclohexane, benzene, n-hexane, toluene and the like, which may be used alone or as a mixture of two or more.

In the production process of the microsphere preparation, a hydrophobic antipsychotic drug is dissolved or dispersed in a solution prepared by dissolving an in vivo histocompatible high molecular weight polymer in a solvent to give an oil layer. The thus obtained oil layer is added to a water layer and subjected to an emulsification treatment to prepare an O/W type emulsion. Thereafter, the microsphere preparation is obtained by removing the solvent in the oil layer by means of an in-water drying method.

When the oil layer is prepared by dispersing a drug, the drug may be used as fine particles. By the use of microcrystals, the surface of microspheres becomes smooth and the drug release becomes close to 0 order. Such a releasing capacity close to 0 order seems to be accomplished due to decrease in the initial releasing rate resulting from the increased interaction between the aforementioned high molecular weight polymer and the drug effected by the increased contacting area and due to an increase in the releasing rate in the late stage effected by the increased surface area of the drug. The finely ground drug may have a particle size of preferably within a range of 10 μm or less, more preferably within a range of 5 μm or less (about 0.1 to about 5 μm, preferably 0.5 to 5 μm). Fine particles of the drug can be obtained by known means, such as use of jet mill, ball mill, vibrating mill, hammer mill, colloid mill and the like.

In preparing microspheres of the present invention, it is preferable to add an emulsifying agent to the water layer, and examples thereof include those which are able to form a stable O/W type emulsion, such as an anionic surfactant (sodium oleate, sodium stearate, sodium lauryl sulfate or the like), a nonionic surfactant (a polyoxyethylene sorbitan fatty acid ester, a polyoxyethylene castor oil derivative or the like), polyvinyl pyrrolidone, polyvinyl alcohol, carboxymethylcellulose, lecithin, gelatin and the like, which may be used alone or as a mixture of two or more. These agents may be used in a concentration of from about 0.01% to about 20%, more preferably from about 0.05% to about 10%.

Removal of the solvent from the oil layer is effected by a conventionally used means [in-water drying method: Tamotsu Kondo, "Maikurokapuseru-sono kinou to ouyou (Microcapsules, Their Functions And Applications)", page 78, Japanese Standards Association, Mar. 20, 1991]. In this method, a solvent is removed by gradually reducing pressure while stirring using a propeller mixer, a magnetic stirrer or the like or by controlling the degree of vacuum using a rotary evaporator or the like.

The thus obtained microspheres are collected by centrifugation or filtration, washed several times with distilled water to remove free drug, the emulsifying agent and the like adhered to the surface of the microspheres and then treated under a reduced pressure, if necessary, with heating, to perfect removal of water and solvent in the microspheres.

If necessary, the thus obtained microspheres are gently ground and screened to remove oversized microspheres. When used as suspensions for injection use, the particle size of the microspheres may be a range which can satisfy their dispersibility and needle-passing property, for example, in the range of from about 0.5 to about 400 μm, more preferably from about 0.5 to about 200 μm, most preferably from about 15 to 50 μm as an average particle size.

The microspheres of the present invention can be made into sustained release injections by preparing an aqueous suspension together with a dispersing agent (polysorbate 80, sodium carboxymethylcellulose, sodium alginate or the like), a preservative (methylparaben, propylparaben, benzyl alcohol, chlorobutanol or the like) and an isotonic agent (sodium chloride, glycerol, sorbitol, glucose or the like) or by preparing an oily suspension by dispersing the microspheres in a plant oil such as olive oil, sesame oil, peanut oil, cotton oil, corn oil or the like or propyleneglycol or the like. In this instance, in order to lessen resistance at the time of injection, the sustained release microsphere preparation of the present invention may be used preferably in the form of an aqueous suspension.

In addition, sustained release injections of microspheres of the present invention can be made into more stable sustained release injections by further mixing the above composition with a filler (mannitol, sorbitol, lactose, glucose or the like), dispersing the mixture and then subjecting the resulting dispersion to freeze drying or spray drying to obtain a solid preparation which can be used by adding distilled water for injection or an appropriate dispersion medium at the time of injection.

Dose of a hydrophobic antipsychotic drug as the active ingredient of the sustained release microsphere preparation of the present invention can be decided depending on each disease to be treated, symptoms and age of each patient and the like, and it may be in the range of generally from 5 to 5,000 mg, preferably from 10 to 2,000 mg, per adult per administration. Since the pharmaceutical preparation of the present invention releases its active ingredient depending on the hydrolysis of the high molecular weight polymer by water, it shows less difference per individual and can be administered by not only intramuscular injection but also subcutaneous injection.

Figure 1:
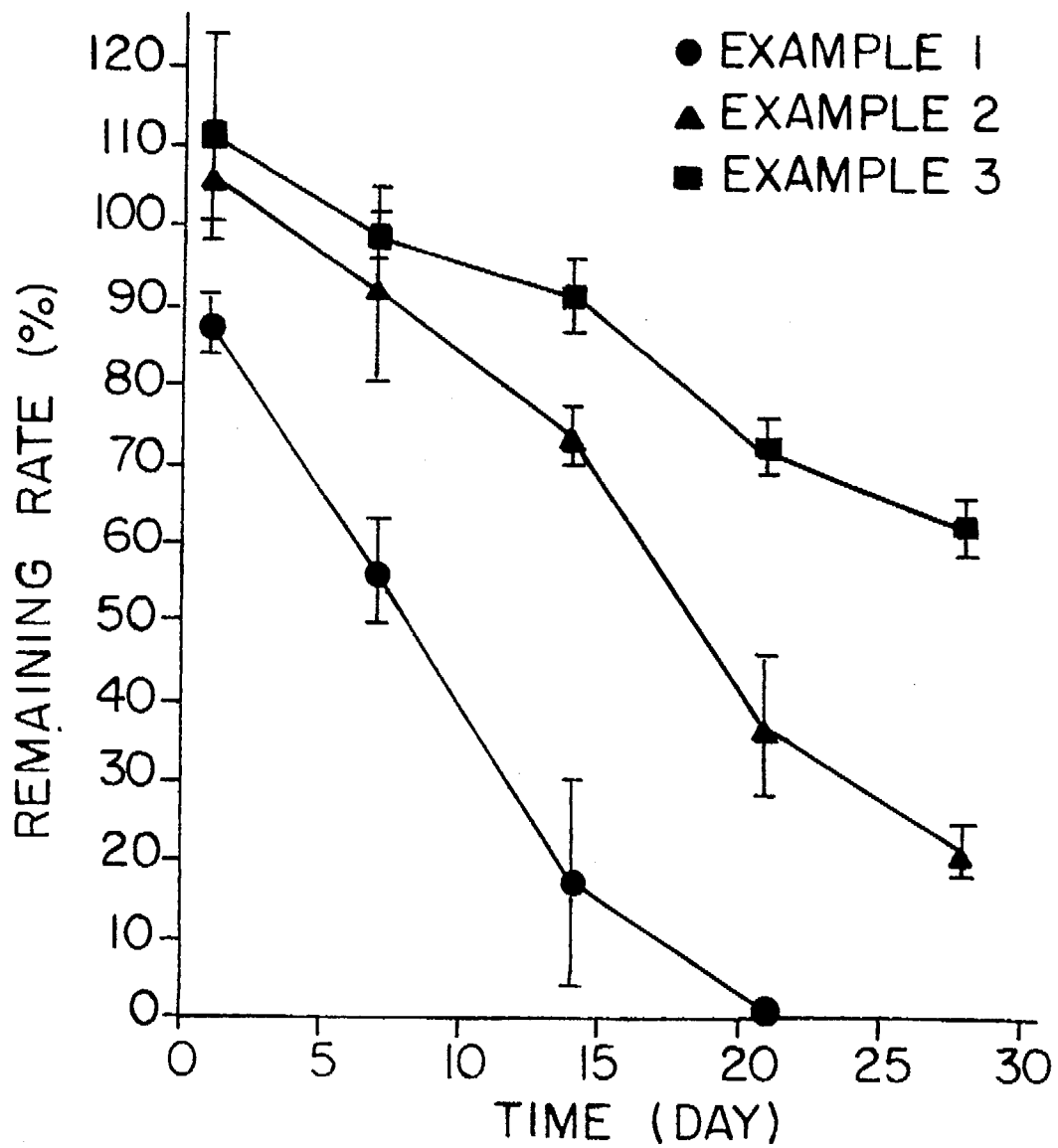
FIG. 1 is a graph showing remaining amount of bromperidol in the administered area of rat after intramuscular injection of each of the microsphere preparations obtained in Examples 1 to 3.

The following Examples and Test Examples are provided to illustrate the present invention in further detail.

EXAMPLE 1

Poly(lactic-co-glycolic)acid (50:50) (molecular weight: about 20,000) was dissolved in 3 ml of dichloromethane to prepare a 40% solution. In this was dissolved 190 mg of bromperidol (average particle size: 13.0 µm) to prepare a mixed solution. This was poured into 1,000 ml of 0.5% polyvinyl alcohol (Gosenol EG-40, manufactured by The Nippon Synthetic Chemical Industry) and dispersed using a homogenizer (manufactured by Tokushu Kika Kogyo) to prepare an O/W type emulsion. Thereafter, the O/W type emulsion was gently stirred using a conventional mixer to effect evaporation of dichloromethane and solidification of microspheres which were subsequently collected by centrifugation, simultaneously washing with distilled water. The thus recovered microspheres, after being made into a powder preparation by freeze drying, had an average particle size of 36.4 µm.

EXAMPLE 2 dl-Polylactic acid (molecular weight: about 10,000) was dissolved in 3 ml of dichloromethane to prepare a 20% solution. In this was suspended 190 mg of bromperidol (average particle size: 2.5 µm) to obtain a mixed solution. Thereafter, a powder preparation was obtained in the same manner as described in Example 1. The bromperidol-containing freeze dried microspheres had an average particle size of 21.4 µm.

EXAMPLE 3 dl-Polylactic acid (molecular weight: about 20,000) was dissolved in 3 ml of dichloromethane to prepare a 20% solution. In this was dissolved 85 mg of bromperidol (average particle size, 13.0 µm) to obtain a mixed solution. Thereafter, a powder preparation was obtained in the same manner as described in Example 1. The bromperidol-containing freeze dried microspheres had an average particle size of 25.5 µm.

EXAMPLE 4 dl-Polylactic acid (molecular weight about 10,000) was dissolved in 4 ml of dichloromethane to prepare a 30% solution. In this was suspended 380 mg of haloperidol (average particle size: 3.0 µm) to obtain a mixed solution. Thereafter, a powder preparation was obtained in the same manner as described in Example 1. The haloperidol-containing freeze dried microspheres had an average particle size of 25.4 µm.

EXAMPLE 5

A microsphere preparation is obtained in the same manner as described in the above Examples using fluphenazine maleate, chlorpromazine, chlorpromazine hibenzoate, sulpiride, carpipramine hydrochloride, carpipramine maleate, clocapramine hydrochloride, mosapramine hydrochloride, risperidone, clozapine, oranzapine or sertindole as the drug.

TEST EXAMPLE 1

Each of the bromperidol-containing microsphere preparations obtained in Examples 1 to 3 was suspended in physiological saline and administered into the femoral muscle of male SD rats (15 weeks of age) in a dose of 12.5 mg as bromperidol. After a predetermined period of time, microspheres which remained in the administered area were periodically recovered to measure remaining amount of bromperidol. As the result, release of the drug at an almost constant rate was confirmed as shown in FIG. 1.

TEST EXAMPLE 2

Figure 2:
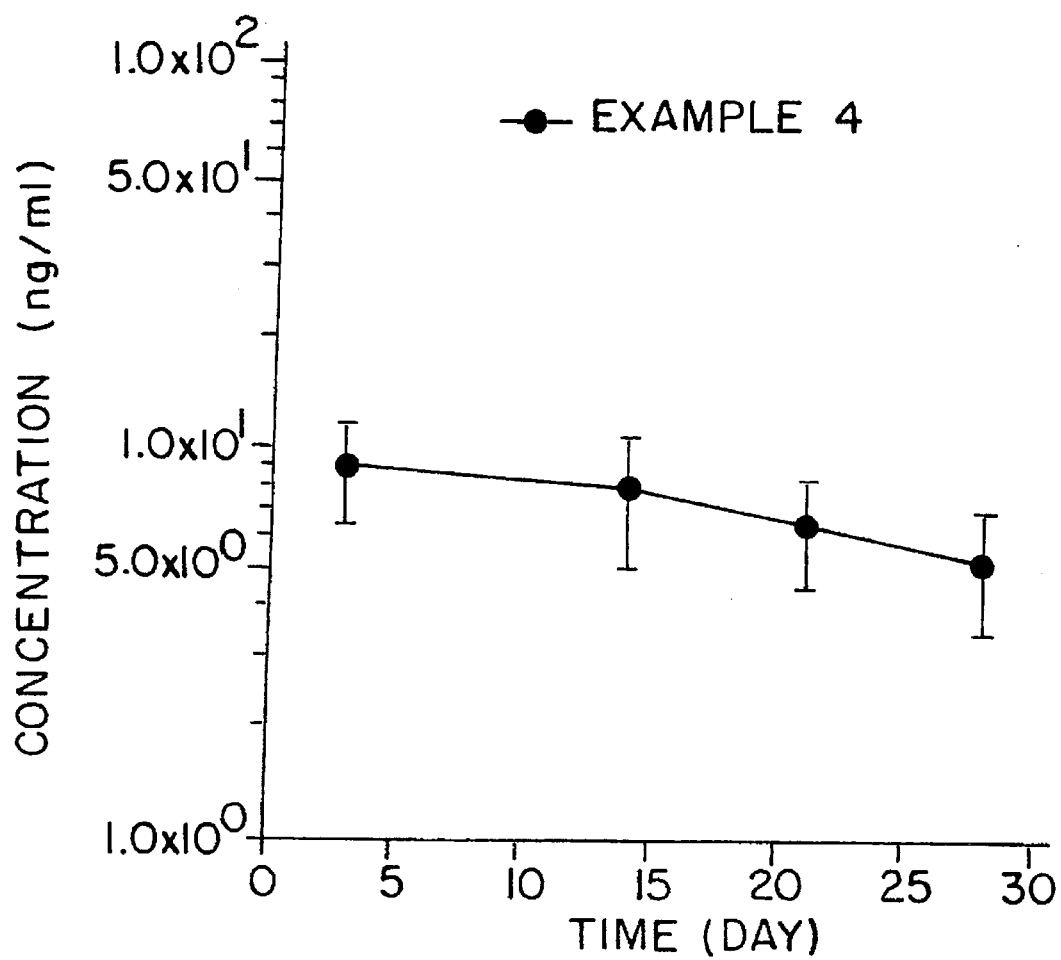
FIG. 2 is a graph showing periodical changes in the drug concentration in blood plasma of rat after intramuscular injection of the haloperidol-containing microsphere preparation obtained in Example 4.

The haloperidol-containing microsphere preparation obtained in Example 4 was suspended in a 0.5% sodium carboxymethyl-cellulose solution isotonized with mannitol and administered into the femoral muscle of male SD rats (13 weeks of age) in a dose of 25 mg as haloperidol. After a predetermined period of time, blood samples were periodically collected from ophthalmic veins to measure concentration of the drug in blood plasma. As the result, sustained concentration of haloperidol in blood plasma was confirmed as shown in FIG. 2.

TEST EXAMPLE 3

Figure 3:
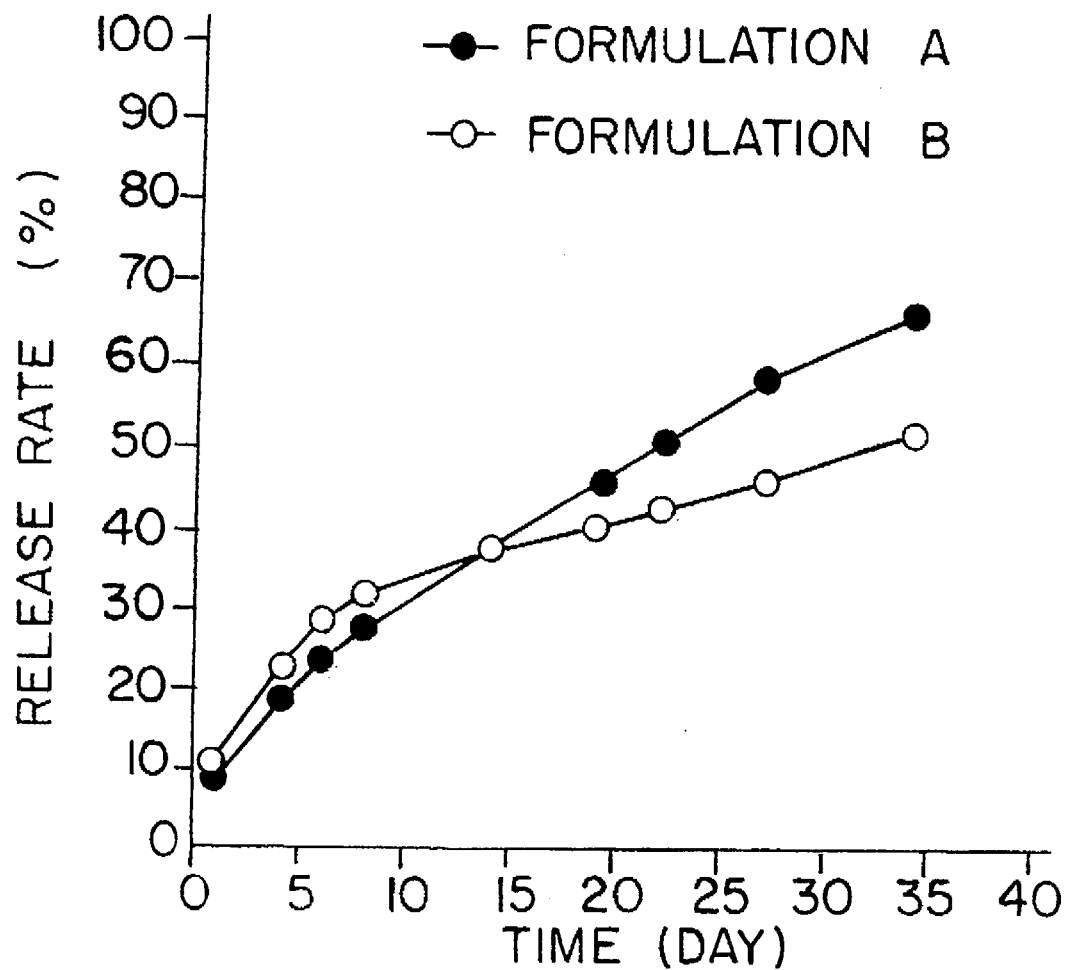
FIGS. 3 and 4 are graphs showing results of an in vitro drug release test of the microsphere preparation obtained in Test Example 3 and Test Example 4, respectively.

A 25 mg portion of each of the bromperidol-containing microsphere preparations obtained from the following Formulations A and B was dispersed in 20 ml of physiological saline and shaken at 37° C. and at 80 revolutions per minute using a constant temperature shaker (manufactured by Yamato Kagaku). Thereafter, samples were periodically collected to calculate drug releasing ratio by ultraviolet absorption photometry (245 nm). As shown in FIG. 3, it was confirmed that the microsphere preparation of Formulation A which comprises finely ground bromperidol can release the drug at a rate of almost 0 order.

FORMULATION A dl-Polylactic acid (molecular weight: about 5,000) was dissolved in 3 ml of dichloromethane to prepare a 12% solution. In this was suspended 190 mg of bromperidol (average particle size: 2.5 µm) to obtain a mixed solution. Thereafter, a bromperidol-containing microsphere preparation was obtained in the same manner as described in Example 1. The freeze dried powder had an average particle size of 19.6 µm.

FORMULATION B

Bromperidol with no grinding (average particle size: 13.0 µm) was used instead of the bromperidol of Formulation A having an average particle size of 2.5 µm. The freeze dried powder, obtained as described in Example 1, had an average particle size of 21.0 μm.

TEST EXAMPLE 4

Figure 4:
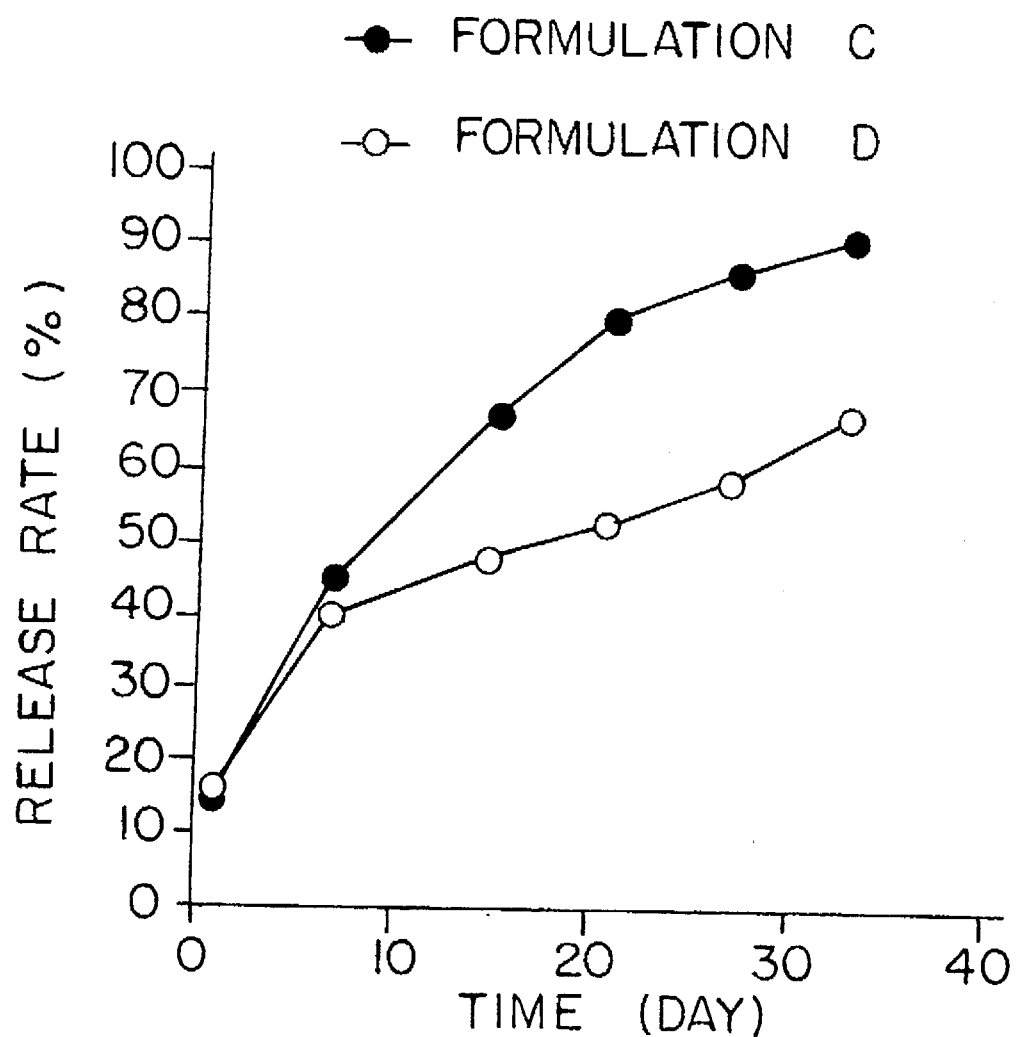

A 15 mg portion of each of the haloperidol-containing microsphere preparations obtained from the following Formulations C and D was dispersed in 20 ml of physiological saline and shaken at 37° C. and at 80 revolutions per minute using a constant temperature shaker (manufactured by Taitech), and samples were periodically collected to calculate drug releasing ratio by ultraviolet absorption photometry (245 nm). As shown in the FIG. 4, it was confirmed that the microsphere preparation of Formulation C which comprises finely ground haloperidol can release the drug at a rate of almost 0 order.

FORMULATION C dl-Polylactic acid (molecular weight: 5,000) was dissolved in 3 ml of dichloromethane to prepare a 12% solution. In this was suspended 190 mg of haloperidol (average particle size: 3.0 μm) to obtain a mixed solution. Thereafter, a freeze dried haloperidol-containing microsphere powder preparation (average particle size: 24.8 μm) was obtained in the same manner as described in Example 1.

FORMULATION D

Haloperidol with no grinding (average particle size: 13.7 μm) was used instead of the haloperidol of Formulation C having an average particle size of 3.0 μm to obtain a freeze dried haloperidol-containing microsphere powder preparation (average particle size: 24.3 μm).

INDUSTRIAL APPLICABILITY

According to the hydrophobic antipsychotic drug-containing sustained release microsphere preparation of the present invention, considerable improvement in compliance in maintenance therapy of mentally deranged persons can be expected because of the following features of the preparation of the present invention.

(1) When a long-term administration is required, desired pharmacological effects can be obtained continuously by one injection per 1 to 8 weeks, instead of daily administration.

(2) Since a biodegradable high molecular weight polymer is used, surgical operations such as embedding and the like are not required at all, and subcutaneous and intramuscular administrations can be made easily absolutely in the same manner as the case of conventional suspension injections so that recovery of the material is not required.

(3) Pain and resistance at the time of administration are small.

Variations of the invention will be apparent to the skilled artisan.

What is claimed is:

1. An antipsychotic drug-containing sustained release microsphere preparation having an almost zero order rate of release when administered to a patient in need thereof and having an average particle size of about 15 to 50 μm, wherein a drug bromperidol or haloperidol is in a form of microcrystals having an average particle size of about 0.5 to 5 μm and is included in a base comprising a high molecular weight polymer having in vivo histocompatibility selected from the group consisting of polylactic acid and poly(lactic-co glycolic)acid.

2. The antipsychotic drug-containing sustained release microsphere preparation according to claim 1, wherein said antipsychotic drug-containing sustained release microsphere preparation is an aqueous suspension.

3. The antipsychotic drug-containing sustained release microsphere preparation according to claim 1, wherein said antipsychotic drug-containing sustained release microsphere preparation is intramuscularly or subcutaneously administered to a patient in need thereof.

4. A process for producing an antipsychotic drug-containing sustained release microsphere preparation having an almost zero order rate of release when administered to a patient in need thereof and having an average particle size of about 15 to 50 μm which comprises making an oil layer comprising a high molecular weight polymer having in vivo histocompatibility selected from the group consisting of polylactic acid and poly(lactic-co-glycolic)acid containing bromperidol or haloperidol in the form of microcrystals having an average particle size of about 0.5 to 5 μm, adding the oil layer to a water layer, subjecting the resulting mixture to an emulsification treatment to obtain an O/W type emulsion and subsequently removing the solvent in the oil layer by an in-water drying method.

* * * * *